Figure 1:
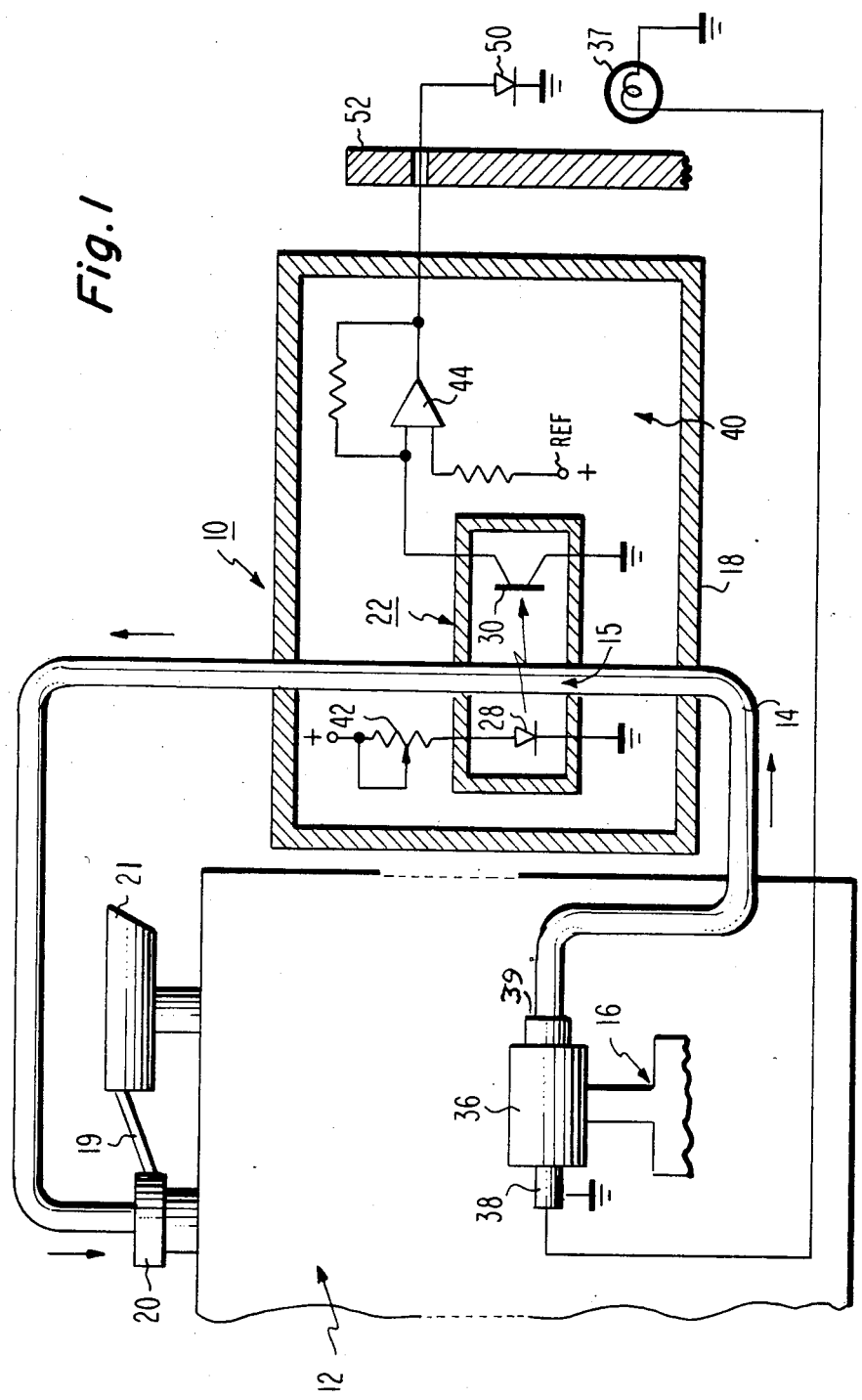

United States Patent [19]

Gager

[11] Patent Number: 4,570,069
[45] Date of Patent: Feb. 11, 1986

[54] ON-BOARD ELECTRONIC OIL CONTAMINATION DETECTOR FOR VEHICLE ENGINES

[76] Inventor: Dennis J. Gager, Pine Ridge, Bear Head Rd., CD #8, Medford, N.J. 08055

[21] Appl. No.: 454,581

[22] Filed: Dec. 30, 1982

[51] Int. Cl.⁴ .................... G01N 21/85; G01N 21/88
[52] U.S. Cl. .................... 250/343; 250/301; 356/70
[58] Field of Search .......... 250/343, 301, 565; 356/70

[56] References Cited

U.S. PATENT DOCUMENTS 3,578,865 5/1971 Traver .................... 356/70
3,790,279 2/1974 Skala .................... 356/70
3,892,485 7/1975 Merritt et al. .................... 356/339

FOREIGN PATENT DOCUMENTS 79210 5/1983 European Pat. Off. ............ 250/301

Primary Examiner—Alfred E. Smith
Assistant Examiner—Constantine Hannaher
Attorney, Agent, or Firm—Morton C. Jacobs

[57] ABSTRACT

An on-board oil quality monitor includes a tube for recirculating oil from an engine, which tube has a transparent portion located within an infra red generator and detector that produces a signal indicating excessive oil contamination when the generated infra red that is transmitted to the detector is below a certain threshold.

6 Claims, 3 Drawing Figures

ON-BOARD ELECTRONIC OIL CONTAMINATION DETECTOR FOR VEHICLE ENGINES

BACKGROUND OF THE INVENTION

This invention relates to the detection of oil contamination in engines and particularly to an electronic detector of oil contamination.

The lubrication of an automobile or other vehicle engine is vital to its usefulness. However, motor oil is contaminated and its lubrication rendered less efficient by oil, oxidation, water, acids, carbon, metal products or dirt. These contaminants reduce the vehicle's performance and serviceable life.

Photoelectric devices for monitoring the motor oil for contamination during vehicle operation are described in U.S. Pat. Nos. 3,578,865 and 3,790,279. However, such devices have not yet achieved general acceptance and widespread use. The need for a detector of oil contamination nevertheless continues.

SUMMARY OF THE INVENTION

It is among the objects of this invention to provide a new and improved oil contamination detector.

Another object is to provide a new and improved oil contamination detector that is effective for continuously monitoring the engine oil.

Another object is to provide a new and improved oil contamination detector that is readily installed in existing equipment.

In accordance with an embodiment of this invention, a contamination detector includes a tube of small diameter for recirculating a small quantity of oil from the engine (e.g. of the crankcase) and back. An intermediate, transparent portion of the tube passes between a light-emitting diode and a phototransistor so that infra red radiation from the diode impinges on the tube and the oil therein. The oil, depending on its state of contamination, absorbs some of the received radiation, and transmits the remainder to the phototransistor. The latter generates a proportional electrical signal that is compared with a threshold value representative of contamination to turn on a warning light when excessive contamination is indicated.

Figure 2:
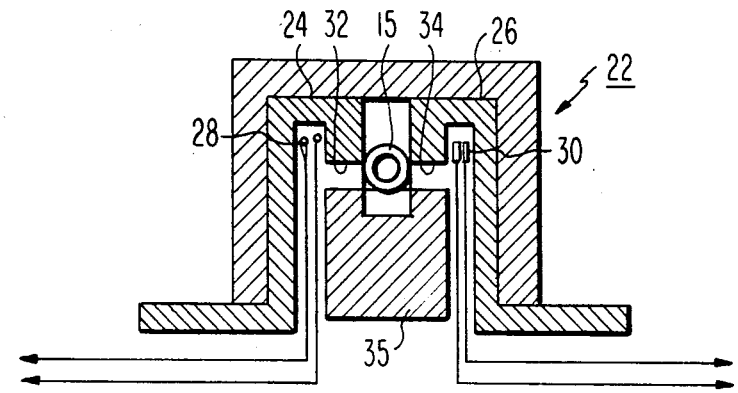
Figure 3:
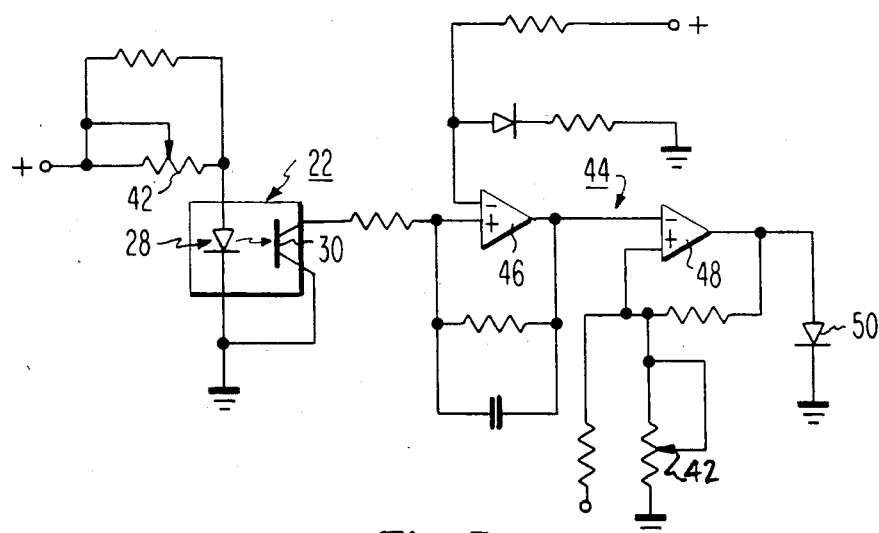

The foregoing and other objects of this invention, the various features thereof, as well as the invention itself, may be more fully understood from the following description when read together with the accompanying drawing in which FIG. 1 is a schematic diagram of an assembled embodiment of the invention in association with an engine whose oil is to be monitored for contamination;

FIG. 2 is a cross-sectional view of an infra red optoelectronic device as assembled in the embodiment of FIG. 1; and FIG. 3 is a schematic circuit diagram of the monitoring electronics of the optoelectronic device of FIG. 1.

In the drawing, corresponding parts are referenced throughout by similar numerals. The various parts of the overall contamination system are shown in disproportionate relation for illustration purposes.

The on-board electronic oil contamination detector 10 of this invention is illustrated in FIG. 1 in association with a vehicle engine 12, only a portion of which is shown. A narrow gauge tube 14 is connected at one end of an oil tap 16 on the engine, passes through a light tight housing 18 containing the electronic monitor and has a return at the other end to the crankcase of the engine. The return may be via a hole in the cap 20 for refilling the oil or replacing the oil filter or through the valve cover of an engine cylinder. Where the oil filter is vented through an air cleaner 21, the venting tube 19 may be used as the oil tube return.

The tube 14 should be small (e.g. ⅛th inch outer diameter) to carry a very small quantity of oil from the pressure center tap 16 on the engine block through a photoelectric or optoelectronic device 22 in the light tight housing 18 and back to the refiller cap 20. The tubing should be flexible to permit unrestricting bending and several feet long to enable locating the electronics housing as remote from the engine as possible. A section 15 of the tube 14 in the photoelectronic device should be transparent to infra red radiation. The entire tube 14 can be transparent since infra red is not likely to be present to interfere with the operation of the photoelectric device 22.

The photoelectric device consists of a plastic block having two opposed opaque enclosures 24 and 26, in which are recessed respectively a light-emitting diode (LED) 28 and a phototransistor 30. The tube is press fitted between the two enclosures 24 and 26, and in the path (which also have two small light passages 32 and 34, respectively) to pass infra red radiation from the diode 28 through the transparent section 15 of the tube 14 to the phototransistor 30. A removable central portion 35 of the plastic block permits a secure assembly of the device 22.

The pressure tap 16, which normally receives oil under pressure from the engine has a threaded connection to which a tee adapter is connected. One outlet of the adapter 36 receives the pressure sender 38 (normally used in tap 16) which supplies an electrical or pressure signal to the vehicle dashboard 52, to light a lamp 37 that indicates an excess pressure and to leave the lamp unlit when the pressure is at a suitable level.

At the other outlet of the tee adapter 36, the tube 14 is connected by a suitable fitting 39. Thereby, when the engine is operating, there is continuously circulating a small quantity of oil from the engine crankcase through the tap 16 and tee adapter 36 and then, via the tube 14, through the photodetector 22 and back to the pressure cap 20 or other suitable return. A printed circuitboard 40 is also mounted in the light tight housing 18. The LED 28 is energized from a suitable voltage source and potentiometer 42 on the printed circuit board 40 and the phototransistor 30 is connected in circuit with a threshold comparison circuit 44 which compares the electrical signal generated by the phototransistor 30 with a suitable threshold signal proportionally representative of a contamination level at which the oil should be changed. Circuit 44 develops an on-off (binary) signal respectively in indicating whether the contamination of the oil is above or below the threshold. This binary signal most suitably can be supplied via connecting lead to a light indicator 50 (e.g. an LED diode), on the dashboard 52 of the vehicle so that the operator can be informed of its state at all times.

The housing 18 is located under the hood of an automobile and in the general vicinity of the engine, but preferably as distant from it as reasonably possible in order to avoid the influence of the engine heat. The circuit board 40 contains an appropriate DC power supply, which in turn is powered from a suitable source of the engine, such as the coil or choke supply.

As shown in the schematic circuit diagram of FIG. 3, the light-emitting diode 28 is energized from a suitable DC voltage source, including a potentiometer 42 whereby the voltage across the diode can be varied for general calibration purposes. The phototransistor 30 supplies its output to the threshold comparison circuit 44 that includes as DC amplifier 46, which generates a voltage proportional to the infra red radiation transmitted to the phototransistor 30. The latter voltage, in turn, is supplied as one input of a comparator circuit 48 which receives the reference voltage that serves as the threshold for comparison. The output of the comparator 48 to drive a suitable indicator shown as an LED 50, is a low voltage which leaves diode 50 unlit when the contamination level is below the acceptable threshold and a high voltage to light the LED when the contamination is above that threshold. A timing circuit (not shown) on circuit board 40 preferably supplies the high voltage momentarily when the ignition is turned on to show that the LED is operable.

In operation when the engine is running, the assembled tubing 14 continuously supplies oil from the crankcase through the photo device for continuous photo-examination of the oil contamination. The oil pressure is sufficient to drive the small quantity of oil through the tubing and provide a continuously changing sample thereof. The scanning LED 28 energized through the power supply to the vehicle, and through a suitable regulated voltage supply source, emits infra red radiation that is transmitted through the transparent portion of the tube 14 and through the oil where it is absorbed by various contaminants. The infra red radiation received by the phototransitor generates an electrical current from which a proportionate voltage is produced by amplifier 46. (A suitable LED/phototransistor combination for the infra red scanning of the oil is MCA8). This voltage is thus proportional to the infra red radiation received by the phototransistor and varies with the absorption by the contaminants.

Among the contaminants in the oil which have a significant deteriorating effect on the oil's quality and which absorb the infra red radiation are antifreeze, glycol, water, varnish, fuel dilution and solids, such as iron, lead, aluminum, silicon, copper, tin and chromium. These contaminants absorb the infra red in varying ways. The net infra red to the phototransistor is that remaining after the cumulative absorption by the contaminants. One or more of the contaminants may predominate, or several may contribute to a contamination level at which the threshold is exceeded. The threshold is set by the reference signal supplied to comparator 48 in conjunction with the setting of potentiometer 42.

The average person (e.g. service station attendant) who periodically looks at the oil level to ensure that it is sufficient, may or may not examine the oil for its contamination. A visual examination only reveals a small factor of the contaminants even to the skilled eye. Feeling the oil may or may not reveal other contaminants to a skilled mechanic. Important segments of contamination would only be revealed in individual laboratory analysis for each contaminant, for example, by refined infra red techniques. The available alternative used in practice is to follow an average oil change regimen recommended by oil or oil-filter manufacturers, or by the vehicle manufacturers. These averages are quite rough in their estimate and cannot account for the variety of conditions that bring about the contamination. In contrast, the continuous infra red scanning of this invention can supply far more information of an estimated cumulative contamination of the variety of contaminants to the operator of a vehicle than can rough averages or skilled eyes or fingers of service station attendants.

When the oil is contaminated to a certain point (represented by the reference signal input to comparator 48, and the setting of potentiometer 42), the infra red radiation received by the phototransistor 30 is correspondingly reduced. At that contamination level, the voltage supplied via the amplifier 46 to the comparator is decreased proportionately, so that the threshold value of the reference is greater than the incoming signal in the comparator 48. The latter then supplies an increased voltage to the LED 50 to light that indicator lamp as a warning that the oil is contaminated to such a degree that it should be changed.

When the contamination threshold is being reached, the visual-light oil quality indicator 50 starts to flicker on and off representing successive samples of oil which have excessive contaminants alternating with those which do not. Generally, this is a good time for the oil to be changed. If it is not, ultimately the oil check indicator will come on steadily indicating that the oil samples are continuously contaminated. The visual indicator is preferred to a sound warning indicator.

In the drawing, the disproportion of parts can be appreciated by recognizing that the dimension of the photo device 22 is less than an inch, and the housing 18 and circuit board 40 are but a couple of inches long. The familiar illustrated parts of the engine are, of course, very much larger.

Thus, in accordance with this invention, a new and improved on-board oil contamination monitor is provided. Various modifications of this invention will be apparent to those skilled in the art from the foregoing description in accordance with the letter and spirit of the accompanying claims.

The continuously scanning oil quality monitor is effective to detect contaminated oil and far more effectively than the human eye, which is ordinarily and practically not able to effectively detect many of the aforementioned contaminants.

What is claimed:

1. An on-board motor-oil-quality monitor for an over-the-road-vehicle engine comprising
    means including a small diameter oil tube for continuously drawing a small quantity of oil from an oil pressure point and recirculating oil back to the engine, said oil tube including a transparent monitor portion, said oil tube being a plurality of feet long and positioning said transparent monitor tube portion at a location remote from the engine, the flow volume of said tube being small compared to the oil capacity of said engine;
    an opaque housing for retaining said transparent monitor rube portion at said remote location;
    said housing including means for mounting a light-emitting device adjacent said transparent monitor tube portion for supplying infra red radiation thereto and for mounting a photodetector adjacent said transparent monitor tube portion for receiving infra red radiation transmitted therethrough and through engine oil circulating therein; said photodetector being characterized by generating an electrical signal representative in magnitude of the infra red radiation from said device and transmitted by the circulating oil and thereby of the cumulative contamination level of the oil;

and means for comparing the magnitude of said electrical signal to a certain threshold signal indicative of a maximum desired cumulative contamination level of the oil and for generating a perceivable signal representative of the contamination level of the oil, so that the contaminated state of the engine oil can be continuously monitored.

2. An on-board motor-oil-quality monitor as recited in claim 1 wherein said oil drawing and recirculating means includes an adapter for conjointly coupling said oil tube and an oil pressure sender to the engine.

3. An on-board motor-oil-quality monitor as recited in claim 1 wherein said opaque housing is located under the hood of the vehicle, and said perceivable-signal generating means is perceivable from the dashboard of the vehicle.

4. An on-board motor-oil-quality monitor as recited in claim 3 wherein said means for comparing signals is located on a circuit board in said housing.

5. An on-board motor-oil-quality monitor as recited in claim 4 wherein said threshold signal is adjustably settable to change the oil contamination level being monitored.

6. An on-board motor-oil-quality monitor as recited in claim 1 wherein said light-emitting device is a light emitting diode and said photodetector is a phototransistor.

* * * * *